July 18, 1972 S. R. SMITH Plant Pat. 3,240
AZALEA PLANT
Filed Jan. 28, 1971
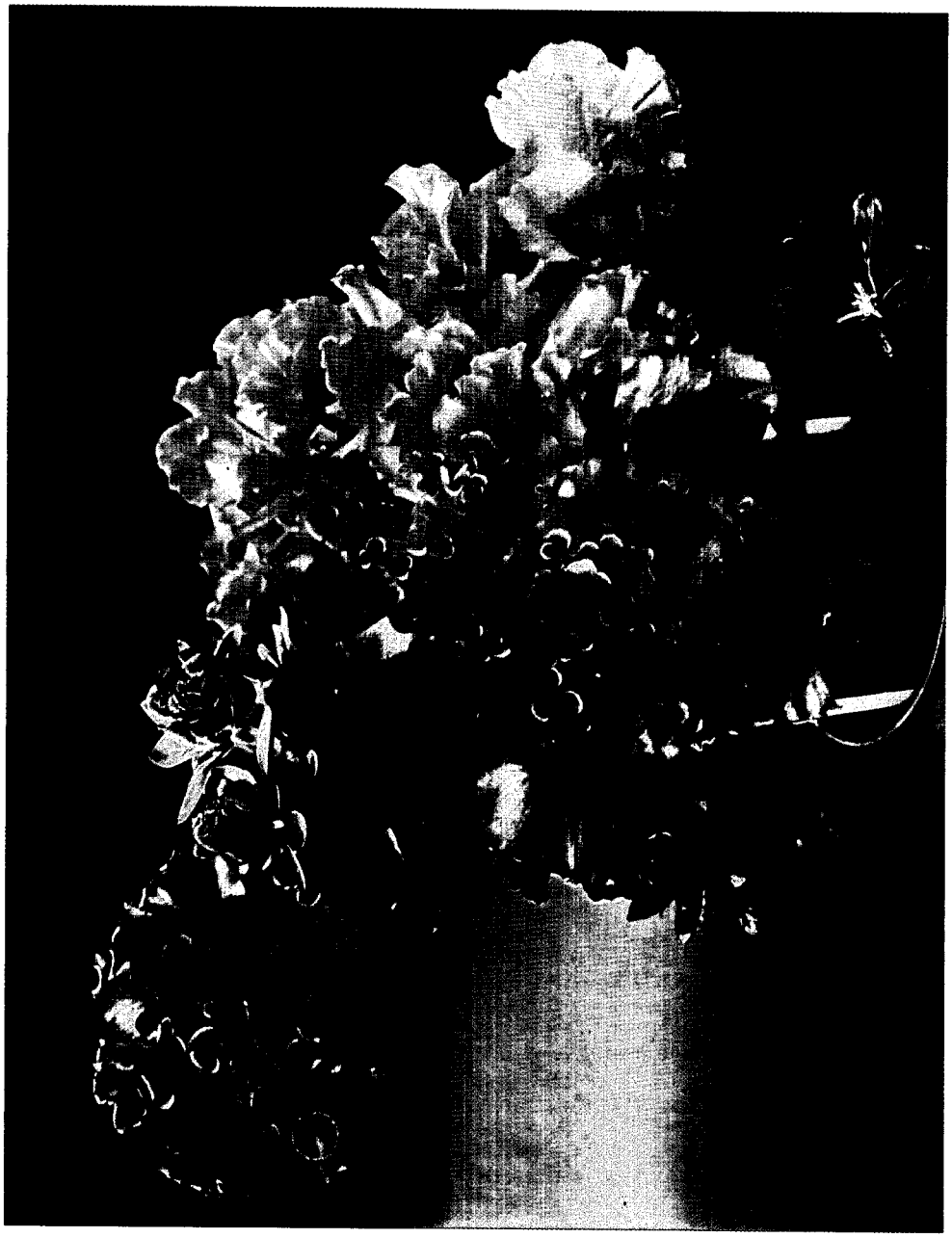
Inventor.
Spencer R. Smith
By: Robb & Robb
Attorneys.

United States Patent Office

Plant Pat. 3,240
Patented July 18, 1972

3,240

AZALEA PLANT

Spencer R. Smith, Rockwood, Mich., assignor to Post Gardens, Inc., Rockwood, Mich.

Filed Jan. 28, 1971, Ser. No. 110,675
Int. Cl. A01h *5/00*
U.S. Cl. Plt.—57 1 Claim

The present invention relates to a new and distinct variety of azalea plant which was discovered by me as a cultivated sport of the azalea variety known as "Big Ben" (Plant Pat. No. 3,041).

At the time of my discovery, many plants of the variety "Big Ben" were being commercially grown under my management and care in the nursery of my assignee located at Rockwood, Mich.

While tending these plants and forcing them into bloom for the Valentine Day market, my attention was attracted to one particular plant which had a branch which bore flowers that were quite different from those on the remainder of that plant, as well as distinct from those of any of the other plants of "Big Ben." In addition to the exceptionally large size of the flowers, the flower color was several shades deeper and a more vibrant red color, and the flower form was even more ruffled in appearance than the flowers of "Big Ben." Upon close inspection of this particular plant, I found that it had sported, and I, thereupon took immediate steps to carefully preserve the sport and keep it under close observation. After my discovery, I asexually reproduced the sport at monthly intervals, as performed by propagating stem cuttings planted, and grown by me in the nursery of my assignee at Rockwood, Mich. Continued observation and tests of the original sport and the progeny thereof derived from the aforementioned cuttings have convinced me that the unusual features initially observed, together with other distincitive features subsequently noted, are established and transmissible through succeeding propagations and represent a unique combination of commercially valuable characteristics which is definitely distinguished from the parent, as well as from all other azalea varieties of which I am aware, as evidence by the following outstanding features thereof:

(1) A vigorous and upright plant habit;
(2) Heavy and strong stems;
(3) Attractive hard and glossy foliage;
(4) Exceptionally large and long flower buds;
(5) A very large open bloom size;
(6) An extremely double-ruffled bloom form; and
(7) A distinctive and attractive, bright, vibrant, deep red flower color.

The accompanying drawing shows a typical specimen plant of my new azalea variety as depicted in color as nearly true as it is reasonably possible to make the same in a color illustration of this character.

The following is a detailed description of the new variety, with color terminology in accordance with Koster's Color Guide, except where general color terms of ordinary dictionary significance are obvious:

Locality where grown and observed: Rockwood, Mich.
Parentage: Sport of "Big Ben."

Propagation: Holds its distinguishing characteristics through succeeding propagations by cuttings.

Plant:
- *Form.*—Bush; upright; branching.
- *Habit.*—Vigorous.
- *Rooting.*—Roots easily and readily; comparable to the variety known as "Chimes" (unpatented).
- *Blooming habit.*—Uniform profuse.
- *Blooming season.*—Mid-season (January, February and March).
- *Suitability for forcing.*—Excellent.
- *Foliage.*—Size: Medium. Quantity: Abundant. Color: New foliage—Color—Fuzzy light yellow-green. Mature foliage—Color—Upper side—Dark glossy green, corresponding to near Holly Green, Plate 82; under side—Light green, corresponding to near Boxwood Green, Plate 79. Shape: Oval pointed. Texture: Upper side—Leathery; glossy. Under side—Smooth. Margin: Smooth. Aspect: Healthy. vigorous. Disease resistance: Comparable to "Chimes" as determined by comparison with other azalea varieties grown under the same conditions at Rockwood, Mich.

Flowers:
- *Borne.*—Several to stem; in regular rounded clusters; on strong stems of medium length.
- *Size.*—Unusually large; average 4½ inches in diameter.
- *Quantity of bloom.*—Abundant, in greenhouse.
- *Continuity.*—One season.
- *Permanence.*—Good.
- *Petalage.*—Number of petals under normal conditions: From 5 to 7 or more. Color: Bright vibrant red, corresponding to near Blood Red, Plate 24. Texture: Thick and durable. Appearance: Flattened bell-shaped, with double-ruffled edges. Arrangement: Profuse, rounded, pyramidal clusters.

Bud: Abnormally large and long.

Reproductive organs:
- *Stamens.*—Similar to parent.
- *Pollen.*—Similar to parent.
- *Styles.*—Similar to parent.
- *Ovaries.*—Similar to parent.

General observations: Most nearly resembles parent variety "Big Ben," but flower color is much darker and a more intense red, and flower edges are more doubly ruffled; heavy strong stems and hardy glossy foliage give impression of vigor and sturdiness; buds are extremely large and longer than most other varieties.

I claim:

1. A new and distinct variety of azalea plant, substantially as herein shown and described, characterized particularly as to novelty by the unique combination of a vigorous and upright plant habit, heavy and strong stems, attractive hard and glossy foliage, exceptionally large and long flower buds, a very large open bloom size, an extremely double-ruffled bloom form, and a distinctive and attractive, bright, vibrant, deep-red flower color.

No references cited.

ROBERT E. BAGWILL, Primary Examiner